United States Patent
Motitschke et al.

Patent Number: 6,060,071
Date of Patent: *May 9, 2000

[54] ECTOIN AND ECTOIN DERIVATIVES AS MOISTURIZERS IN COSMETICS

[75] Inventors: Lothar Motitschke, Hilden; Hansjürgen Driller, Monheim; Erwin Galinski, Bonn, all of Germany

[73] Assignee: Merck Patent GmbH, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/953,988

[22] Filed: Oct. 20, 1997

Related U.S. Application Data

[63] Continuation of application No. 08/746,253, Nov. 7, 1996, abandoned, which is a continuation of application No. 08/355,275, Dec. 12, 1994, abandoned.

[30] Foreign Application Priority Data

Dec. 12, 1993 [DE] Germany ............... 43 42 560

[51] Int. Cl.$^7$ .................................................. A61K 7/48
[52] U.S. Cl. .......................................... 424/401; 514/847
[58] Field of Search ........................... 424/401; 514/847

[56] References Cited

U.S. PATENT DOCUMENTS

| | | | |
|---|---|---|---|
| 2,649,397 | 5/1953 | Ballard | 167/33 |
| 5,047,409 | 9/1991 | Di Schiena | 514/275 |
| 5,403,845 | 4/1995 | Dunbar | 514/275 |

FOREIGN PATENT DOCUMENTS

| | | |
|---|---|---|
| 0 088 542 | 9/1983 | European Pat. Off. |
| 0 553 884 | 8/1993 | European Pat. Off. |
| 2 132 079 | 1/1973 | Germany |
| 2 154 948 | 5/1973 | Germany |
| 94/15923 | 7/1994 | WIPO |

OTHER PUBLICATIONS

European Search Report dated Jul. 14, 1995.
Patent Abstracts of Japan—Japanese Patent No. JP-A-03031265, vol. 15, No. 154.
Patent Abstracts of Japan—Japanese Patent No. JP-A-03086867, vol. 15, No. 259.
Galinski et al., "1,4,5,6-Tetrahydro-2-methyl-4-pyrimidinecarboxylic acid" Eur. J. Biochem, 149, pp. 135–139 (1985).
Derwent Patent Abstract No. An 90-161349 of Japanese Patent No. JP-A-2104577.
STN CHemical Abstract No. 115:15263 CA of Mita "Application of betaine to cosmetics and its toxicity" Frangrance J., 19(2) 70–7 (1991).
Galinski et al., "1,4,5,6-Tetrahydro-2-methyl-4-pyrimidinecarboxylic Acid," Eur. J. Biochem. 149, 1985, pp. 135–139.
B. Idson, "Dry Skin Moisturizing and Emolliency," Cosmetics & Toiletries, vol. 107, 1992, pp. 69–78.
Severin et al., "The Predominant Role of Recently Discovered Tetrahydro-pyrimidines For The Osmoadaptation of Halophilic Eubacteria," Journal of General Microbiology 138, 1992, pp. 1629–1638.

*Primary Examiner*—Thurman K. Page
*Assistant Examiner*—S. Tran
*Attorney, Agent, or Firm*—Finnegan, Henderson, Farabow, Garrett & Dunner, L.L.P.

[57] ABSTRACT

Cosmetic preparations for the care of aged, dry or irritated skin are prepared using a compound of the formula Ia or Ib

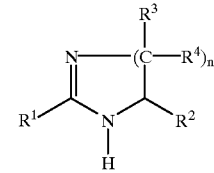

(Ia)

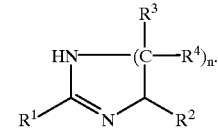

(Ib)

2 Claims, No Drawings

ECTOIN AND ECTOIN DERIVATIVES AS MOISTURIZERS IN COSMETICS

This application is a continuation of application Ser. No. 08/746,253 filed Nov. 7, 1996, which is a continuation of 08/355,275, filed Dec. 12, 1994, both now abandoned.

DESCRIPTION

It is known that (S)-1,4,5,6-tetrahydro-2-methyl-4-pyrimidinecarboxylic acid (ectoin) is found in extremely halophilic microorganisms and that it plays a role in the osmoregulation of these organisms (E. A. Galinski et al., Eur. J. Biochem., 149 (1985) pages 135–139).

A major task of cosmetics is the preservation or restoration of the normal state of the skin. In addition to other criteria, stabilizing the moisture content of the skin plays an important role. Under normal conditions, the skin itself is capable of regulating its moisture content. A change in the external environment, such as, for example, a cold dry atmosphere, very rapidly results in the state in which the skin surface is dried out. The surface of the skin turns flaky and tends to chap slightly. The skin is highly sensitive to chemical and physical factors. In patients suffering from atopy, these skin symptoms are observed irrespectively of the age, while, in healthy humans, the dry skin condition becomes more pronounced as they grow older (B. Idson, Cosmetics & Toiletries, 107 (1992), pages 69–78). This skin condition can be prevented as well as counteracted by using suitable moisturizing preparations.

The ingredients used for this purpose in moisturizing preparations differ with regard to two, different principles of action. The occlusive substances (for example paraffin oils) form a barrier on the skin surface which is impermeable to water vapor, whereby they prevent trans-epidermal water loss (TEWL) of the skin. In contrast, intradermal substances such as glycerol bind the water in the skin.

It has now been found that cosmetic preparations comprising at least one compound of the formula Ia or Ib improve and stabilize the hydration of the human skin.

The invention relates to the use of at least one compound of the formula Ia or Ib

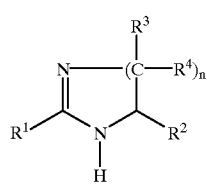

(Ia)

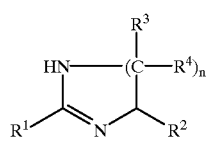

(Ib)

and/or a physiologically acceptable salt of the compound of the formula Ia or Ib and or a stereoisomeric form of the compound of the formula Ia or Ib for the preparation of cosmetic products; $R^1$ being defined as follows:
  a) a hydrogen atom or
  b) $(C_1-C_4)$-alkyl, $R^2$ being defined as follows:
  a) a hydrogen atom,
  b) —COOH, c) 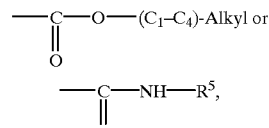

d) 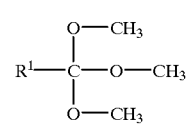

in which $R^5$ is
  1) a hydrogen atom,
  2) $(C_1-C_4)$-alkyl,
  3) an amino acid radical,
  4) a dipeptide radical or
  5) a tripeptide radical, $R^3$ and $R^4$ independently of one another being defined as follows:
  a) a hydrogen atom or
  b) —OH, and
  n is the number 1, 2 or 3.

The compounds of the formula Ia or Ib can be present in the cosmetic products in the form of the optical isomers, diastereomers, racemates, zwitterions, cations or in the form of a mixture of these.

Preferred is the use of at least one compound of the formula Ia or Ib, $R^1$ being defined as follows:
  a) a hydrogen atom or
  b) methyl, $R^2$ being defined as follows:
  a) a hydrogen atom or
  b) —COOH, $R^3$ and $R^4$ independently of one another being defined as follows:
  a) a hydrogen atom or
  b) —OH, and
  n is the number 2.

The invention furthermore relates to cosmetic products comprising (S)-1,4,5,6-tetrahydro-2-methyl-4-pyrimidinecarboxylic acid and/or (S,S)-1,4,5,6-tetrahydro-5-hydroxy-2-methyl-4-pyrimidinecarboxylic acid.

The invention furthermore relates to processes for the preparation of the compound of the formula Ia or Ib which comprise A) reacting a compound of the formula II

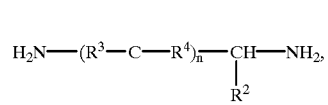

(II)

in which $R^1$ is as in formula Ia, with a compound of the formula III $$H_2N—(R^3—C—R^4)_n—CH—NH_2,$$
                              $|$
                              $R^2$ (III)

in the presence of an alcohol to give a compound of the formula Ia or Ib, $R^3$, $R^4$ and n being defined as in formula Ia and $R^2$ being a hydrogen atom or —COOH, or B) reacting a compound of the formula Ia or Ib in which $R^2$ is —COOH with an alkyl halide to give the corresponding carboxylic esters of the compound of the formula Ia or Ib, or C) reacting a compound of the formula Ia or Ib in which $R^2$ is an activated carboxylic ester with an amine of the formula $NH_2$—$R^5$ to give the corresponding carboxamide of the compound of the formula Ia or Ib.

The term "amino acid" is to be understood as meaning the stereoisomeric forms, for example the D and L forms of the following compounds: asparagine, arginine, aspartic acid, glutamine, glutamic acid, β-alanine, γ-aminobutyrate, Nε-acetyllysine, Nδ-acetylornithine, Nγ-acetyldiaminobutyrate, Nα-acetyldiaminobutyrate, histidine, isoleucine, leucine, methionine, phenylalanine, serine, threonine and tyrosine. L-amino acids are preferred. Amino acid radicals are derived from the corresponding amino acids.

The following amino acid radicals are preferred: Gly, Ala, Ser, Thr, Val, β-Ala, γ-aminobutyrate, Asp, Glu, Asn, Gln, Nε-acetyllysine, Nδ-acetylornithine, Nγ-acetyldiaminobutyrate, Nα-acetyldiaminobutyrate.

The amino acids are abbreviated as is generally customary. The di- or tripeptide radicals are acid amides by their chemical nature and disintegrate into two or three amino acids upon hydrolysis. The amino acids in the di- or tripeptide radical are linked to each other by amide linkage.

Examples of suitably physiologically acceptable salts of the compound of the formula Ia or Ib are, for example, alkali metal salts, alkaline earth metal salts or ammonium salts, such as the sodium salt, potassium salt, magnesium salt, calcium salt, triethylamine salt or tris(2-hydroxy-ethyl) amine salt. Other physiologically acceptable salts of the compound of the formula Ia or Ib result from reaction with inorganic acids such as hydrochloric acid, sulfuric acid and phosphoric acid or with organic carboxylic or sulfonic acids such as acetic acid, citric acid, benzoic acid, maleic acid, fumaric acid, tartaric acid and p-toluenesulfonic acid. Compounds of the formula Ia or Ib in which the same number of basic and acidic groups, such as carboxyl or amino groups, exist, form internal salts.

The invention furthermore relates to a process for the preparation of di- or tripeptides or the salts thereof, which comprises a) reacting a segment with a C-terminal free carboxylic group or an activated derivative thereof with a suitable segment with an N-terminal free amino group, or b) synthesizing the di- or tripeptide stepwise, and, if appropriate, eliminating one or more protective groups in the compound obtained by a) or b) which have been introduced temporarily for protecting other functions and, if appropriate, converting the resulting compounds to a physiologically acceptable salt thereof.

The di- or tripeptides are prepared stepwise starting from the C-terminal end or by coupling segments, following the general methods of peptide chemistry (Houben-Weyl, Methoden der Organischen Chemie [Methods in Organic Chemistry], Volume 15/1,2). The peptide coupling steps can be effected for example by the mixed anhydride method, by active radicals or azides or by the carbodiimide method, in particular with the addition of substances which accelerate the reaction and prevent racemisization, such as 1-hydroxybenzotriazole, N-hydroxysuccinimide, 3-hydroxy-4-oxo-3,4-dihydro-1,2,3-benzotriazine, N-hydroxy-5-norbornene-2,3-dicarboximide, furthermore using active derivatives of 1-hydroxybenzotriazole or anhydrides of phosphoric acids, phosphonic acids and phosphinic acids, at a reaction temperature of −10° C. to the boiling point of the solvent, preferably from −5° C. to 40° C.

Suitable solvents are dimethylformamide, dimethylacetamide, N-methylpyrrolidone or dimethyl sulfoxide. Solvents such as methylene chloride, chloroform or tetrahydrofuran may also be employed if the reactants are sufficiently soluble.

If it is required to prevent secondary reactions or if required for the synthesis of specific peptides, the functional groups in the side chain of amino acids are additionally protected by suitable protecting groups, the following being employed in the main: Arg(Tos), Arg(Mts), Arg(Mtr), Arg(PMV), Asp(OBzl), Asp(OBut), Cys(4-MeBzl), Cys(Asm), Cys(SBut), Glu(Obzl), Glu(Obut), His(Tos), His(Fmoc), His(Dnp), His(Trt), Lys(Cl-Z), Lys(Boc), Met(O), Ser(Bzl), Ser(But), Thr(Bzl), Thr(But), Trp(Mts), Trp(CHO), Tyr(Br-Z), Tyr(Bzl) or Tyr(But).

Amino protecting groups which are preferably used are the benzyloxycarbonyl (Z) radical which can be eliminated by means of catalytic hydrogenation, the 2-(3,5-dimethyloxyphenyl) propyl(2)oxycarbonyl (Ddz) radical or trityl (Trt) radical which can be eliminated by means of weak acids, and the 9-fluorenylmethyloxycarbonyl (Fmoc) radical which can be eliminated by means of secondary amines.

In process variant A), a procedure is best followed in which the compound of the formula II is reacted in an equimolar amount or in an excess of up to three times in an inert solvent, such methanol, ethanol or isopropanol with a compound of the formula III (in the dihydrochloride form) with constant stirring to give a compound of the formula Ia or Ib. The reaction temperatures are 30 to 90° C., or 30° C. to the boiling point of the solvent, preferably 40 to 70° C., in particular around 55° C.

The reaction times are from 15 minutes to 48 hours, preferably from 30 minutes to 3 hours, particularly preferably from 1 to 2 hours. The end of the reaction can be determined for example by means of HPLC.

To isolate and purify the reaction products of the formula Ia or Ib, the solvent may be distilled off, the dried reaction mixture may be neutralized in demineralized water with acids or bases, and zwitterionic products may be purified on an ion retardation column (for example the type BIORAD® AG11A8) using demineralized water as the eluent. To purify cationic products, they are bound to a cation exchanger in the H⁺form and eluted for example using a perchloric acid gradient.

The resulting compound of the formula Ia or Ib in which $R^2$ is —COOH is converted to the corresponding carboxylic ester (process variant B) for example by dissolving 1 g of the hydrochloride of the compound of the formula Ia or Ib in 20 ml of 0.2 NHCl in methanol, refluxing the mixture for 2 hours and subsequently evaporating it under reduced pressure. As is the case with nitrophenyl esters, the esterification reaction is accelerated by addition of equimolar amounts of dicyclohexylcarbodiimide as a water-binding agent.

The corresponding carboxamides of the formula Ia or Ib (process variant C) can be obtained by dissolving 1 g of activated carboxylic ester (for example of the p-nitro-phenyl ester) of the compound of the formula Ia or Ib in 250 ml of dichloromethane and reacting the mixture with gaseons $NH_3$ or with the corresponding amino acid or with a di- or tripeptide (with an addition of triethylamine). The reaction can be monitored with the aid of the p-nitrophenolate which forms (development of a yellow color).

The starting compounds of the process variant A) are known or can be obtained commercially. (S)-1,4,5,6-tetrahydro-2-methyl-4-pyrimidinecarboxylic acid or (S,S)-1,4,5,6-tetrahydro-5-hydroxy-2-methyl-4-pyrimidine-carboxylic acid can also be obtained microbiologically (Severin et al. J. Gen. Microb. (1992), 138, pages 1629–1638).

The cosmetic product is prepared by formulating at least one compound of the formula Ia or Ib and/or one physiologically acceptable salt of the compound of the formula Ia or Ib, if appropriate together with auxiliaries and/or carrier substances, to give a suitable formulation. The auxiliaries and carrier substances belong to the group of the carriers, preservatives and other customary auxiliaries.

The cosmetic products based on the compound of the formula Ia or Ib are used externally.

Examples of use forms which may be mentioned are: solutions, suspensions, emulsions, pastes, ointments, gels, creams, lotions, powders, soaps, surfactant-containing cleansers, oils and sprays. In addition to the compound of the formula Ia or Ib, any desired customary carrier substances, auxiliaries and, if appropriate, other active substances are added to the product.

Auxiliaries to be preferred belong to the group of the preservatives, antioxidants, stabilizers, solubilizers, vitamins, colorants and odor improvers.

In addition to the compound of the formula Ia or Ib, ointments, pastes, creams and gels may comprise the customary carrier substances, for example animal and vegetable fats, waxes, paraffins, starch, tragacanth, cellulose derivatives, polyethylene glycols, silicones, bentonites, silica, talc and zinc oxide or mixtures of these substances.

In addition to the compound of the formula Ia or Ib, powders and sprays may comprise the customary carrier substances, for example lactose, talc, silica, aluminum hydroxide, calcium silicate and polyamide powder, or mixtures of these substances. Sprays may additionally comprise the customary propellants, for example chlorofluorohydrocarbons, propane/butane or dimethyl ether.

In addition to the compound of the formula Ia or Ib, solutions and emulsions may comprise the customary carrier substances, such as solvents, solubilizers and emulsifiers, for example water, ethanol, isopropanol, ethyl carbonate, ethyl acetate, benzyl alcohol, benzyl benzoate, propylene glycol, 1,3-butylglycol, oils, in particular cottonseed oil, groundnut oil, maize germ oil, olive oil, castor oil and sesame seed oil, glycerol fatty acid esters, polyethylene glycols and fatty acid esters of sorbitan or mixtures of these substances.

In addition to the compound of the formula Ia or Ib, suspensions may comprise the customary carrier substances, such as liquid diluents, for example water, ethanol or propylene glycol, suspending agents, for example ethoxylated isostearyl alcohols, polyoxyethylene sorbitol esters and polyoxyethylene sorbitan esters, microcrystalline cellulose, aluminum metahydroxide, bentonite, agar-agar and tragacanth or mixtures of these substances.

In addition to the compound of the formula Ia or Ib, soaps may comprise the customary carrier substances, such as alkali metal salts of fatty acids, salts of fatty acid hemiesters, fatty acid protein hydrolyzates, isethionates, lanolin, fatty alcohol, vegetable oils, plant extracts, glycerol, sugars or mixtures of these substances.

In addition to the compound of the formula Ia or Ib, surfactant-containing cleansing products may comprise the customary carrier substances, such as salts of fatty alcohol sulfates, fatty alcohol ether sulfates, sulfo-succinic monoesters, fatty acid protein hydrolyzates, isethionates, imidazolinium derivatives, methyltaurates, sarcosinates, fatty acid amide ether sulfates, alkyl-amidobetaines, fatty alcohols, fatty acid glycerides, fatty acid diethanolamides, vegetable and synthetic oils, lanolin derivatives, ethoxylated glycerol fatty acid esters or mixtures of these substances.

In addition to the compound of the formula Ia or Ib, facial oils and body oils may comprise the customary carrier substances, such as synthetic oils, such as fatty acid esters, fatty alcohols, silicone oils, natural oils such as vegetable oils and oily plant extracts, paraffin oils, lanolin oils or mixtures of these substances.

Other characteristic use forms in cosmetology are lipsticks, lipsalve sticks, mascara, eyeliner, blusher, powder foundation, emulsion foundation and wax foundation, and also suncare and after-sun preparations.

The active concentration of the compound of the formula Ia or Ib in the cosmetic product according to the invention amounts to 0.1 to 10% by weight, preferably 0.1 to 3% by weight.

The invention furthermore relates to the use of the compound of the formula Ia or Ib for the preparation of cosmetic products for the care and prophylaxis of dry and/or irritated skin and of dry flaky scalp, in particular for increasing and/or stabilizing the moisture content of the skin.

EXAMPLE 1

Preparation of (S)-1,4,5,6-tetrahydro-2-methyl-4-pyrimi-dinecarboxylic acid 60 ml of trimethyl orthoformate are dissolved in 400 ml of methanol, and reacted with 30 g of L-diaminobutyric acid×2 HCl at 55° C. with constant stirring. After a reaction time of 2 hours, the solvent is evaporated under reduced pressure, the crude product which remains is dissolved in 50 ml of demineralized water, and the solution is neutralized using NaOH. The compound is subsequently purified on an ion retardation column type BIORAD® AG11A8 (Bio-Rad Laboratories GmbH, Munich, Germany) using demineralized water as the eluent, and the product is dried and recrystallized from methanol. The compound obtained can be identified by means of high-pressure liquid chromatography (HPLC); (for example E. Merck, Darmstadt, Germany, LiChroCART® 125-NH$_2$ 5µ, eluent: 80% acetonitrile), and is characterized by the following $^{13}$C-NMR data: 176.8, 161.2, 53.8, 37.9, 22.0, 18.7 ppm (relative to TMS); (Galinski E. A., Pfeiffer H. P., Truper H. G. (1985) Eur. J. Biochem. 149, 135–139).

EXAMPLE 2

Cosmetic activity

A) Water absorption capacity

The water absorption capacity of the compound of Example 1 is determined at a relative atmospheric humidity of 65%. The control substances used are in each case glycerol and propylene glycol. In each case 1 g of the anhydrous substance is kept in a sealed chamber until the weight is constant. The water absorption capacity is calculated as follows:

$$\text{Water absorption in \%} = \frac{\text{Weight of the amount of water absorbed}}{\text{Weight of the dried substance}} \times 100$$

Ectoin has a water absorption of 25% and, in comparison with glycerol or propylene glycol (60 and 45%, respectively) a less pronounced hygroscopic behavior. However, with regard to its use as a moisturizer, the dehydrating effect known from unduly high glycerol concentrations can be ruled out.

B) Hydration of the human skin

The hydration is measured capacitively using the Corneometer® CM 820 (Courage & Khazaka Electronic GmbH).

Here, the relatively high dielectric constant of water is exploited. The end face of the sensor contains the measuring capacitor. When the measuring head is pressed against the skin, the horny layer reaches the scatter area of the capacitor field. The changes in capacity differ as a function of the water content. The short measuring time rules out errors caused by deformation of the skin or evaporation build-up.

The forearm of 7 test subjects is treated once daily for 14 days with an emulsion comprising (S)-1,4,5,6-tetrahydro-2-methyl-4-pyrimidinecarboxylic acid (compound of Example 1, ectoin). As a control, the corresponding placebo emulsion is applied to the other forearm. The data determined by the Corneometer demonstrate that the hydration of human skin which has been treated with the emulsion according to the invention is approximately 10% higher than by direct comparison with the placebo emulsion. This means that the hydration of the human skin is markedly improved and significantly higher than the hydration achieved with the placebo emulsion.

The composition of the emulsions is shown in Table 1.

TABLE 1

| Placebo emulsion | |
|---|---|
| A potassium cetyl phosphate | 3.0% |
| A glyceryl stearate | 4.0% |
| A methoxy PEG-17/dodecyl glycol copolymer | 1.0% |
| A glyceryl laurate | 2.0% |
| A ceteraryl alcohol | 3.0% |
| A steareth-21 | 0.3% |
| A polymethyl methacrylate | 1.0% |
| A isocetyl alcohol | 6.0% |
| A macadamia nut oil | 2.0% |
| A dimethicone | 2.0% |
| A caprylic/capric triglyceride | 4.0% |
| A perfluoropolymethyl isopropyl ether | 0.5% |
| A butylhydroxytoluene | 0.02% |
| B purified water | 61.23% |
| B sodium carbomer | 0.25% |
| B sorbeth-30 | 3.0% |
| B glycerol | 2.0% |
| B methyl gluceth-20 | 0.5% |
| B ethylene diamine-N,N,N',N'-tetraacetic acid, tetrasodium salt | 0.05% |
| B panthenol | 2.0% |
| B preservative | 1.9% |
| B magnesium aluminum silicate | 0.15% |
| C perfume | 0.1% |
| (S)-1,4,5,6-tetrahydro-2-methyl-4-pyrimidinecarboxylic acid (ectoin emulsion) | |
| A potassium cetyl phosphate | 3.0% |
| A glyceryl stearate | 4.0% |
| A methoxy PEG-17/dodecyl glycol copolymer | 1.0% |
| A glyceryl laurate | 2.0% |
| A ceteraryl alcohol | 3.0% |
| A steareth-21 | 0.3% |
| A polymethyl methacrylate | 1.0% |
| A isocetyl alcohol | 6.0% |
| A macadamia nut oil | 2.0% |
| A dimethicone | 2.0% |
| A caprylic/capric triglyceride | 4.0% |
| A perfluoropolymethyl isopropyl ether | 0.5% |
| A butylhydroxy toluene | 0.02% |
| B purified water | 60.23% |
| B sodium carbomer | 0.25% |
| B sorbeth-30 | 3.0% |
| B glycerol | 2.0% |
| B methyl gluceth-20 | 0.5% |
| B ethylene diamine-N,N,N',N'-tetracetic acid tetrasodium salt | 0.05% |
| B panthenol | 2.0% |
| B preservative | 1.9% |
| B magnesium aluminum silicate | 0.15% |

TABLE 1-continued

| C perfume | 0.1% |
|---|---|
| D (S)-1,4,5,6-tetrahydro-2-methyl-4-pyrimidine carboxylic acid | 1.0% |

We claim:

1. A method of treating a patient suffering from aged, dry or irritated skin or of dry, flaky scalp, comprising administering to said patient an effective amount of of at least one compound selected from compounds of the formula Ia or Ib:

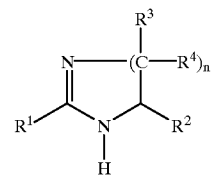

(Ia)

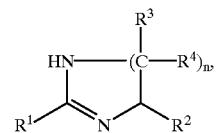

(Ib)

physiologically acceptable salts thereof and steroisomeric forms thereof effective to treat aged, dry, or irritated skin or dry flaky scalp by hydrating the skin or scalp, together with a cosmetically acceptable carrier;

$R^1$ being defined as follows:
  a) a hydrogen atom or
  $(C_1-C_4)$-alkyl, $R^2$ being defined as follows:
  a) a hydrogen atom, b) —COOH, c) —C(=O)—O—$(C_1-C_4)$-Alkyl, or d) —C(=O)—NH—$R^5$, in which $R^5$ is
  1) a hydrogen atom,
  2) $(C_1-C_4)$-alkyl,
  3) an amino acid radical,
  4) a dipeptide radical or
  5) a tripeptide radical, $R^3$ and $R^4$ independently of one another being defined as follows:
  a) a hydrogen atom or
  b) —OH and
  n is the number 1, 2, or 3.

2. A method of increasing or stabilizing the moisture content of a patient's skin, comprising administering to said patient an effective amount of at least one compound selected from compounds of the formula Ia or Ib:

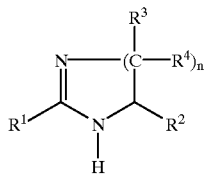 (Ia)

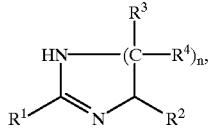 (Ib)

physiologically acceptable salts thereof and steroisomeric forms thereof effective to treat aged, dry, or irritated skin or dry flaky scalp by hydrating the skin or scalp, together with a cosmetically acceptable carrier;

$R^1$ being defined as follows:
 a) a hydrogen atom or
 $(C_1-C_4)$-alkyl, $R^2$ being defined as follows:
 a) a hydrogen atom,
 b) —COOH,
 c) 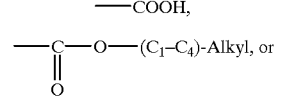
 d) 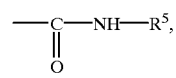

in which $R^5$ is
 1) a hydrogen atom,
 2) $(C_1-C_4)$-alkyl,
 3) an amino acid radical,
 4) a dipeptide radical or
 5) a tripeptide radical, $R^3$ and $R^4$ independently of one another being defined as follows:
 a) a hydrogen atom or
 b) —OH and n is the number 1, 2, or 3.

* * * * *